United States Patent [19]

Lee, Jr.

[11] Patent Number: 4,838,283

[45] Date of Patent: Jun. 13, 1989

[54] ANTI-BRUXISM DEVICE

[76] Inventor: Alexander Y. Lee, Jr., 1075 S. Jefferson St., Apt. 321, Arlington, Va. 22204

[21] Appl. No.: 120,359

[22] Filed: Nov. 13, 1987

[51] Int. Cl.⁴ .............................................. A61F 5/56
[52] U.S. Cl. .................................... 128/777; 128/897; 128/905; 128/859; 73/582; 340/573
[58] Field of Search ................. 128/660.06, 24 A, 774, 128/777, 782, 846, 859, 861, 897, 905; 73/582; 340/573, 575

[56] References Cited

U.S. PATENT DOCUMENTS

| | | | |
|---|---|---|---|
| 4,052,977 | 10/1977 | Kay | 128/24 A |
| 4,076,969 | 2/1978 | Sacks | 369/91 |
| 4,114,612 | 9/1978 | Benjamin | 128/76 R |
| 4,169,473 | 10/1979 | Samelson | 128/136 |
| 4,198,542 | 4/1980 | Ducommun | 128/774 |
| 4,220,142 | 9/1980 | Rosen et al. | 128/136 |
| 4,304,227 | 12/1981 | Samelson | 128/136 |
| 4,593,686 | 6/1986 | Lloyd et al. | 128/136 |
| 4,669,477 | 6/1987 | Ober | 128/782 |

*Primary Examiner*—Max Hindenburg
*Assistant Examiner*—Randy Citrin
*Attorney, Agent, or Firm*—Jerry C. Lyell

[57] ABSTRACT

An apparatus and method for the control and prevention of bruxing (nocturnal teeth grinding) which comprises a sound generating means affixed to one area of the face of the user, a sound receiving means affixed to another area of the face, and an electronic control means to "read" signals from said sound receiver and to activate an alarm when bruxing occurs. Said apparatus utilizes the principle of bone conduction whereby the sonic vibrations from said second generator are transmitted to said sound receiver bottom when the jaw of the user is closed than when it is open. The alarm develops a conditioned reflex in the user such that after the first few alarms incident to bruxing the user does not awaken but merely reacts by relaxing the jaw when the alarm occurs.

3 Claims, 2 Drawing Sheets

ANTI-BRUXISM DEVICE

BACKGROUND OF THE INVENTION

Bruxism is the condition of nocturnal teeth grinding which afflicts many people and which is widely considered to be a psychological stress reaction. The condition produces abnormal wear of the molar teeth of the afflicted person and is a source of annoyance and disturbance to anyone who sleeps in the near vicinity of such a person.

Several devices have been patented which were designed to relieve the condition of bruxism. Among such devices are the Samelson inventions, U.S. Pat. Nos. 4,169,473 and 4,304,227. These inventions consist of molded devices designed to be inserted into the mouth of a person who experiences snoring and bruxism during sleep. The object of these inventions is to prevent nocturnal teeth grinding by means of an intervening physical barrier and to prevent snoring by means of forced nasal breathing.

Another device, the Ober invention, U.S. Pat. No. 4,669,477 is an electronic instrument which operates by detecting electromyographic signal voltages from the mandibular musculature during bruxing. The device then imparts an electrical stimulation to the jaw of the bruxing person, which stimulation is intended to cause the jaw muscles to relax and allow the jaw to open. The Ober disclosure does not, however, reveal how said stimulation will selectively stimulate the particular muscle fibers that cause the jaw to open rather than resulting in the tonus of all the muscle fibers in the region of the stimulation.

The existing devices have obvious shortcomings in both design and effect, some of which are overcome by the relative simplicity of the present invention which uses the principle of bone conduction to activate an alarm signal which then develops a conditioned reflex to interrupt the bruxing pattern with a minimum of mental or physical intrusion.

SUMMARY OF THE INVENTION

The present invention is a novel apparatus and method for the control and prevention of bruxism (nocturnal teeth grinding). The apparatus comprises sound generating and receiving means which can be affixed (for example with adhesive) to appropriate locations on the face of a person who experiences bruxism and jaw clenching while sleeping. The device operates on the principle that sonic vibrations travel much better through relatively rigid bone and dental tissue than through softer tissue such as ligaments. For the purpose of conducting or transmitting sound an open or unclenched mandible is "soft coupled" to the skull by means of ligaments and muscle while a closed or clenched mandible is "hard coupled" to the skull. Thus, if the sound generating means is affixed to the side of the face and the sound receiving means is affixed along the side of the jaw, the amplitude of sonic vibrations transmitted to the receiving means will be greater when the jaw is closed than when the jaw is open. The amplitude of sonic vibrations transmitted between the face and jaw can therefore be used to detect the occurance of bruxism in a sleeping person.

Alternately, the sound generating means can be affixed to the jaw and the sound receiving means affixed to the side of the face or even the bridge of the nose with the same result.

In operation the sound generating means and sound receiving means are connected to an electronic control system such that sound waves of any desired frequency or amplitude can be transmitted to the face of a sleeping person via the sound generator (transducer). The tranmitted vibrations are then transduced by the sound receiving means with the resultant signal being amplified, rectified, further amplified and electronically integrated to produce a waveform whose amplitude will activate an audible alarm device when teeth clenching occurs. The electronic control system can produce signals that will result in the sound generated being in either the ultrasonic or subsonic ranges and will therefore be inaudbile to the user of the device.

The alarm need not necessarily be an audible one. It could include flashing lights or any other sensory stimulus.

The electronic control system is further designed to detect the characteristic clenching pattern or "clenching frequency" of the person who experiences bruxism so that miscellaneous signals and noise do not activate the alarm system.

An alternate design of the invention utilizes a monostatic or single sound generating means attached to the face of the sleeping person. For a signal of given amplitude and frequency being supplied to the sound generator, the measurable impedance will vary depending upon whether the person's jaw is open or closed. Comparison measurements of the impedance can be made with a device such as an impedance bridge. Variations in impedance can then be screened by the electronic control system to detect bruxing and to sound the alarm system.

The use of an audible alarm to alert the sleeping person when teeth clenching occurs will not result in significant disturbance of the periods of sleep. The decibel level of the alarm means can be set to an intensity just sufficient to awaken the sleeping person on the first few occasions of teeth clenching. The initial experiences of responding to the alarm will result in the development of a conditioned relfex such that after the user has adapted briefly to the device, then the sounding of the alarm will stimulat the user to relax and unclench the teeth without returning to a state of consciousness. The principles of establishing spinal reflex arcs are well understood by experimenters and practitioners of psychology and operant conditoning.

BRIEF DESCRIPTION OF THE DRAWINGS

The invention may be further understood by reference to the drawings in which.

DESCRIPTION OF THE PREFERRED EMBODIMENT

Figure 1:
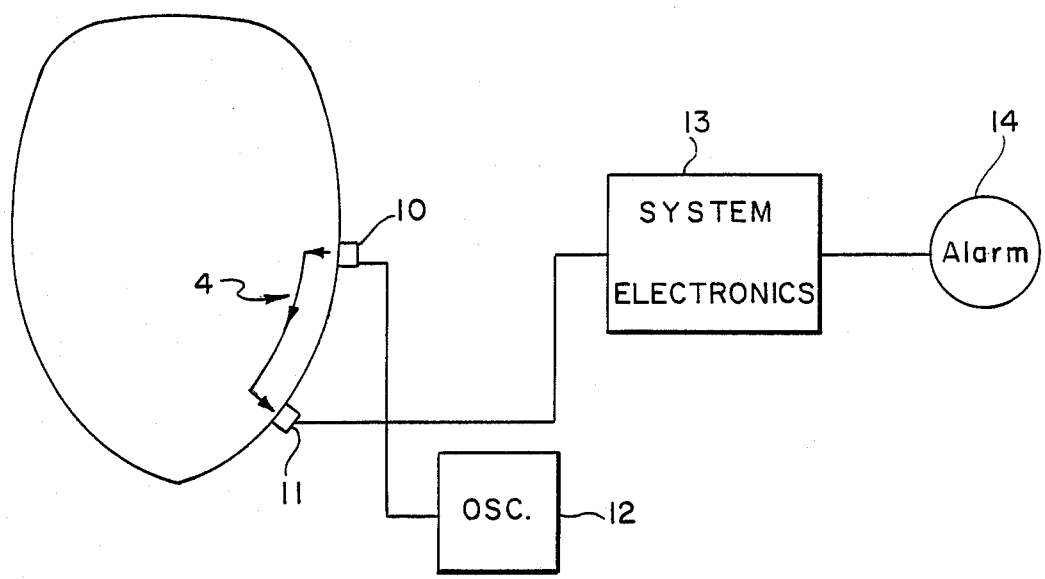
FIG. 1 is a sketch of the various elements of the invention in relation to the user.

Referring now to FIG. 1 of the drawings, one configuration of the invention can be seen wherein the sound generating means 10 is positioned on the side of the face between the eye and the ear of the user. The sound receiving means 11 is positioned along the side of the jaw of the user. Alternately, the sound generating means 10 can be positioned near the bridge of the nose or on the opposite side of the head. In any case, the user of the device would position these two elements so as to maximize the transmission of sonic vibrations 4 through bone and dental tissues rather than through the air. The sound generating and receiving means are electro-mechanical transducers which are old in the art.

In operation, a signal generator 12 such as an oscillator produces an electrical signal of any desired frequency which is imput into the sound generator 10. The sonic vibrations that are produced radiate differentially through the various tissues of the face and skull. Some of the sonic vibrations reach the sound receiver 11 which then transduces the mechanical vibration back into electrical signals. These electrical signals are amplified, demodulated, further amplified, rectified and integrated by the electronic control system 13 to produce a voltage level that activates an audible alarm 14 when bruxing or teeth clenching occurs.

It is the object of the electronic control system 13 to discriminate between the signal amplitude when no bruxing is occurring and the signal amplitude when bruxing is occurring and then to trigger an alarm in response to the bruxing signal.

Figure 2:
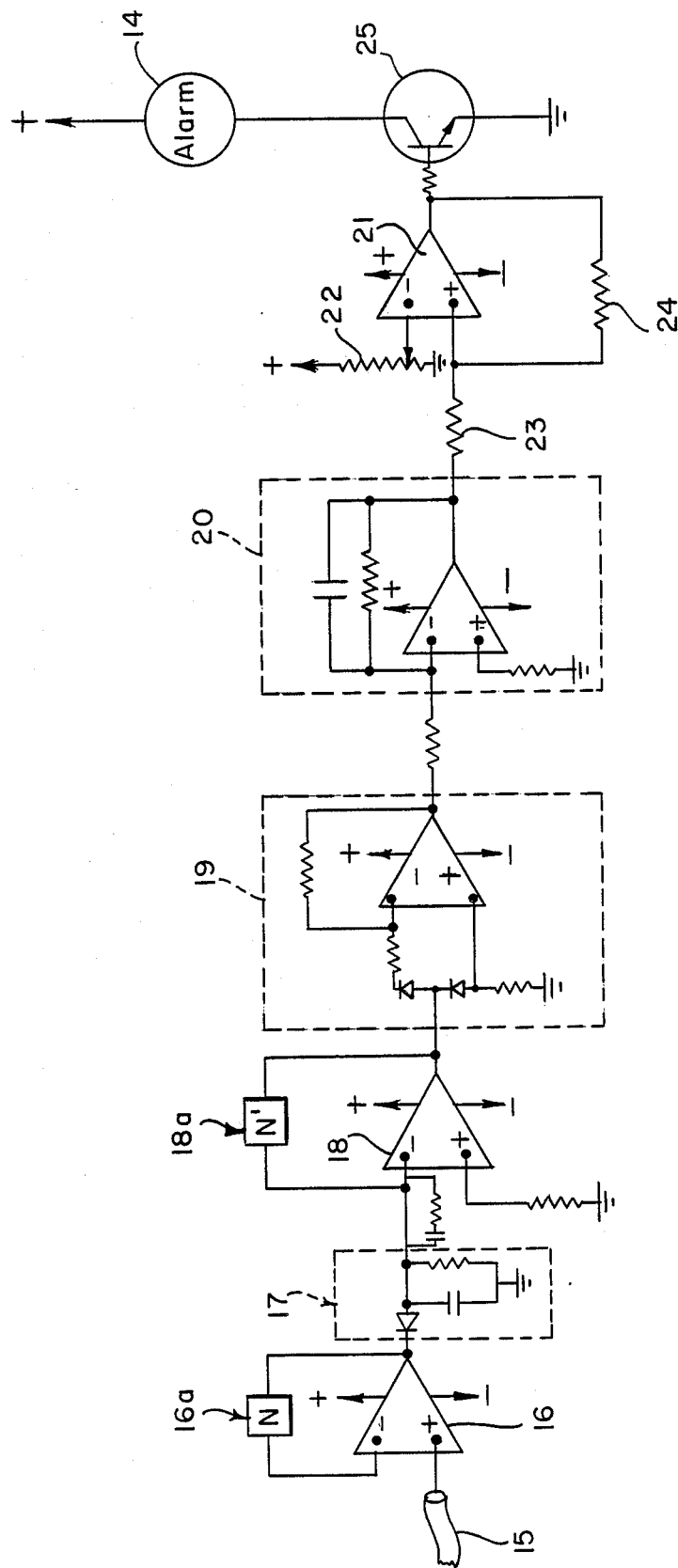
FIG. 2 is a partial schematic diagram of the elements of the electronic control system.

FIG. 2 is a detailed drawing showing the subsystems of the electronic control system 13. A shielded cable 15 conveys the electrical signal from the sound receiver 11 to a first amplifier 16 which preferrably includes a feedback network 6A. Said first amplifier 16 has a relatively narrow passband centered at the sonic operating frequency.

The amplified signal is demodulated by a peak detector diode and network 17 to derive the "clenching frequency", that is, the characteristic frequency of the upper and lower teeth coming together during bruxing. For example, if involuntary opening and closing of the jaw occurs on the average of once each second, then the peak detector diode will recover a one Hz square wave that passes to the second amplifier 18 and feedback network 18A which has a passband to accomodate the "clenching frequency".

The signal from said second amplifier 18 then passes to a full-wave rectifier 19, thence to an electronic integrator 10. Said integrator 20 builds up to the trigger level of switch 21 when substantial bruxing occurs but discriminates against "transients" or stray signals.

Switch 21 has a trigger level and hysteresis determined by the values of a potentiometer 22, input resistance 23 and positive feedback resistance 24. Because of said hysteresis a threshhold bruxing signal will result in switch 21 remaining closed for a finite period of time. The resultant signal then passes through n-p-n transistor 25 and activates alarm 14 for a sufficient period of time to alert the sleeping user that bruxing is occurring.

Figure 3:
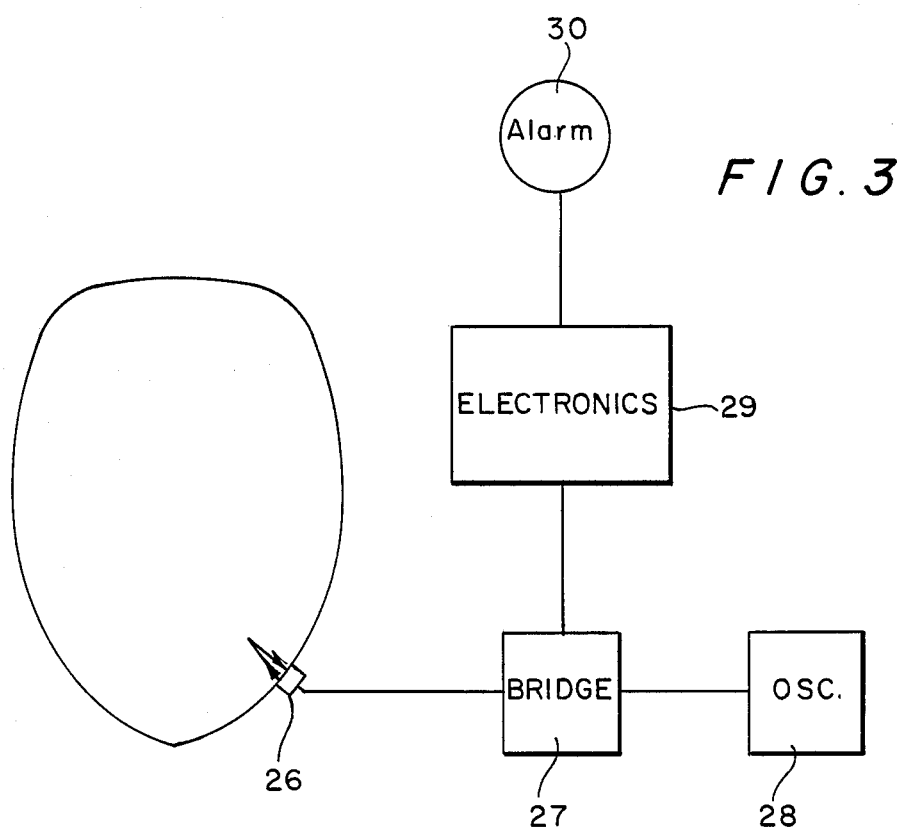
FIG. 3 is a sketch of the elements of the monostatic embodiment of the invention in relation to the user.

Another embodiment of the invention, a monostatic arrangement, is shown in FIG. 3. In this embodiment a sound generating means 26 is positioned as shown on the jaw of the user. A signal generating means 28 supplies signal voltage to sound generator 26 which introduces sonic vibration into the jaw of the user. The impedance to this voltage signal is a function of sound loading by the bone and tissue. The impedance will characteristically vary for a given signal voltage as the jaw is opened and closed. Said impedance is measured by an impedance comparison means 27 such as an impedance bridge. Said impedance measuring means is located on-line between the signal generator 28 and the sound generator 26. Variations in current flow through the impedance measuring means produce voltage variations which are processed by an electronic control system 29 with the same design criteria as control system 13 previously discussed.

Control system 29 activates an alarm 30 when bruxing occurs.

I claim:

1. An apparatus for the control and prevention of bruxing of a subject comprising:
    sound generating means adapted to be mounted on one of a subject's lower jaw or bony structure connected to the upper jaw for generating a sound,
    sound receiving means adapted to be mounted on the other of the subject's lower jaw or bony structure connected to the upper jaw for receiving the sound generated by said sound generating means and for producing a signal voltage in response thereto,
    alarm means for alerting the subject when bruxing occurs, bruxing causing a characteristic amplitude of said generated sound to be received,
    electronic control means for activating said alarm means when said sound generating means generates a predetermined signal voltage in response to a received sound which is at said characteristic amplitude, and
    an adjustable electrical signal generator means for transmitting a signal to said sound generating means.

2. The apparatus as recited in claim 1 wherein said electronic control means includes a first amplifier, a peak detector means, a second amplifier, a full-wave rectifier, an electronic signal integrator and a switching means.

3. An apparatus as recited in claim 2 wherein said switching means has a built-in hysteresis characteristic.

* * * * *